(12) United States Patent
Schreyer et al.

(10) Patent No.: US 7,762,976 B2
(45) Date of Patent: Jul. 27, 2010

(54) AUTOMATIC AIR REMOVAL SYSTEM

(75) Inventors: Johann Schreyer, Munich (DE); Erwin Knott, Poing (DE); Andreas Hahn, Berg (DE)

(73) Assignee: Sorin Group Deutschland GmbH (DE)

( * ) Notice: Subject to any disclaimer, the term of this patent is extended or adjusted under 35 U.S.C. 154(b) by 459 days.

(21) Appl. No.: 10/586,060

(22) PCT Filed: Jan. 20, 2005

(86) PCT No.: PCT/EP2005/000536
§ 371 (c)(1),
(2), (4) Date: Dec. 29, 2006

(87) PCT Pub. No.: WO2005/067998
PCT Pub. Date: Jul. 28, 2005

(65) Prior Publication Data
US 2007/0160495 A1   Jul. 12, 2007

(30) Foreign Application Priority Data
Jan. 20, 2004   (EP) .................................. 04001073

(51) Int. Cl.
*A61M 37/00*   (2006.01)
(52) U.S. Cl. .................... 604/6.09; 604/4.01; 604/5.01; 604/6.1; 604/6.14; 604/6.15; 604/7; 604/65; 604/67; 604/73; 604/405; 604/406; 600/16; 600/17; 600/18; 210/738; 210/741; 210/744; 210/799; 210/805; 422/44; 422/45; 422/47
(58) Field of Classification Search ................ 604/4.01, 604/5.01, 6.09, 6.1, 6.14
See application file for complete search history.

(56) References Cited

U.S. PATENT DOCUMENTS

| 3,507,395 | A | 4/1970 | Bentley |
| 4,490,331 | A | 12/1984 | Steg |
| 4,643,713 | A | 2/1987 | Viitala |
| 5,055,198 | A | 10/1991 | Shettigar |

(Continued)

FOREIGN PATENT DOCUMENTS

EP   1086712   *   7/2000

(Continued)

OTHER PUBLICATIONS

Machine translation of WO 00/28394, Industrial Property Digital Library (26 pages).
Summary of WO 00/28394 (1 page).

*Primary Examiner*—Tatyana Zalukaeva
*Assistant Examiner*—Ilya Y Treyger
(74) *Attorney, Agent, or Firm*—Wolf, Greenfield & Sacks, P.C.

(57) ABSTRACT

An apparatus for extracorporeal oxygenation of a patient's blood during cardiopulmonary bypass surgery. The apparatus comprises a bubble sensor, arranged at or connected to a venous line, for detecting bubbles in the venous blood received from the patient. When air bubbles are detected, a second pump is activated to draw air from an air chamber provided in an air filter connected to the venous line and arranged downstream of the bubble sensor. A first pump draws the blood from the air filter and supplies the blood to an oxygenator and to the patient via an arterial line.

4 Claims, 3 Drawing Sheets

U.S. PATENT DOCUMENTS

| | | | |
|---|---|---|---|
| 5,158,533 A | 10/1992 | Strauss et al. | |
| 5,162,102 A | 11/1992 | Nogawa et al. | |
| 5,205,153 A | 4/1993 | Hlavinka et al. | |
| 5,270,005 A | 12/1993 | Raible | |
| 5,770,149 A * | 6/1998 | Raible | 422/46 |
| 5,876,611 A | 3/1999 | Shettigar | |
| 6,302,860 B1 | 10/2001 | Gremel et al. | |
| 6,337,049 B1 | 1/2002 | Tamari | |
| 6,503,451 B2 * | 1/2003 | Ikeda et al. | 422/45 |
| 6,524,267 B1 | 2/2003 | Gremel et al. | |
| 6,632,189 B1 | 10/2003 | Fallen et al. | |
| 6,723,283 B2 * | 4/2004 | Ghelli et al. | 422/45 |
| 6,960,322 B2 * | 11/2005 | Stringer et al. | 422/45 |

FOREIGN PATENT DOCUMENTS

| | | |
|---|---|---|
| EP | 1086712 A2 | 3/2001 |
| EP | 1203592 A2 | 5/2002 |
| EP | 1374929 A1 | 1/2004 |
| WO | WO 00/28394 A1 | 5/2000 |

* cited by examiner

AUTOMATIC AIR REMOVAL SYSTEM

FIELD OF THE INVENTION

This invention relates to a method and an apparatus for extracorporeal oxygenation of a patient's blood during cardiopulmonary bypass surgery, and more particularly to an automatic air removal system.

BACKGROUND OF THE INVENTION

During cardiopulmonary bypass surgery the patient's blood is pumped through an extracorporeal blood circuit conventionally comprising a venous drainage line, a venous reservoir, a blood pump, an oxygenator, and an arterial filter. Blood is drained from the patient through the venous drainage line into the venous reservoir. The blood pump draws blood from the reservoir and supplies the blood to the patient via the oxygenator and the arterial filter. The venous reservoir as well as the arterial filter removes air bubbles from the blood, which may otherwise pose a serious risk to the patient's life if returned to the patient in the arterial blood flow.

To avoid the venous reservoir an extracorporeal blood circuit may comprise, as described in U.S. Pat. No. 6,524,267, an arterial filter especially adapted to comprise an air chamber, an purge port having an increased size for allowing a vacuum to actively purge air from the air chamber, a check valve being incorporated into the purge port to prevent air or blood from a cardiotomy reservoir from being drawn into the arterial filter by the negative pressure in the arterial filter, when the purging vacuum is not active, and an air sensor being connected to activate the purge vacuum when, and only when, air is present in the air chamber of the arterial filter.

Arterial filters are known in the art, for example from U.S. Pat. No. 5,632,894, U.S. Pat. No. 4,676,771, U.S. Pat. No. 4,572,724, and U.S. Pat. No. 4,411,783. However, conventional air filters cannot be used in the above second extracorporeal blood circuit although it would be cost saving if conventional components can be used in setting up extracorporeal blood circuit.

SUMMARY OF THE INVENTION

The present invention provides a method and an apparatus for extracorporeal oxygenation of a patient's blood during, for example, cardiopulmonary bypass surgery, without the necessity to provide a venous reservoir, improved in that conventional arterial filters may be used thereby avoiding the necessity to provide adapted components.

DESCRIPTION OF THE PREFERRED EMBODIMENTS

Figure 1:
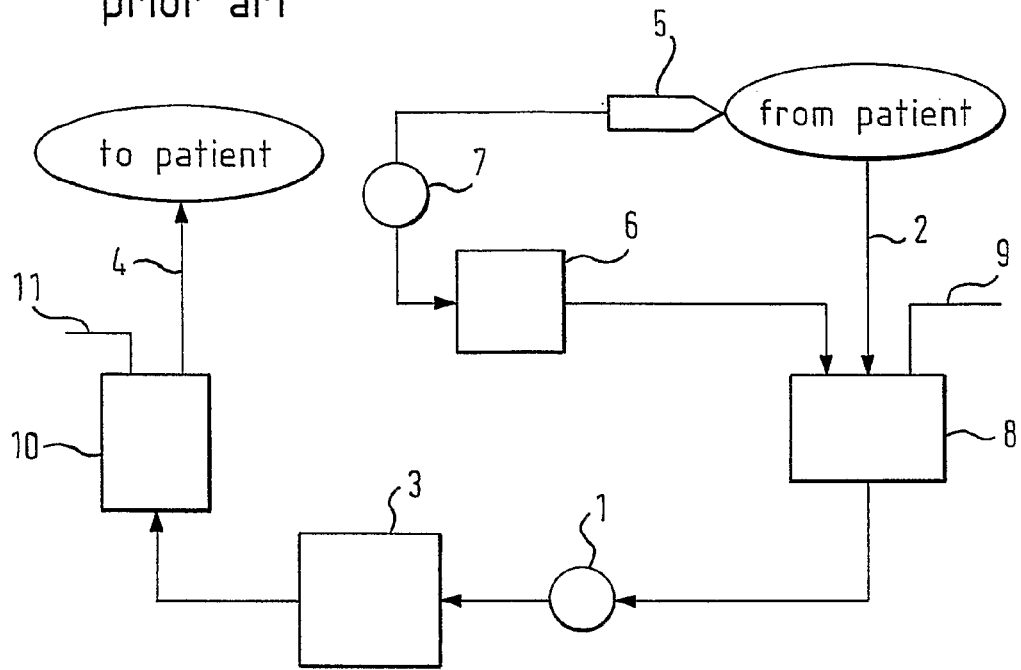
FIG. 1 is a schematic diagram of a first conventional apparatus for extracorporeal oxygenation of a patient's blood.

As schematically shown in FIG. 1, a conventional heart-lung equipment comprises pump means 1 for drawing the blood of a patient during cardiovascular surgery through a venous line 2 and supplying it to an oxygenator 3. The oxygenated blood is returned to the patient through an arterial line 4. Cardiotomy blood is collected by a suction device 5 and is delivered to a cardiotomy reservoir 6 by a suction pump 7 connected to the suction device 5.

In the above conventional extracorporeal blood circuit, venous blood from the venous line 2, as well as defoamed and filtered cardiotomy blood from the cardiotomy reservoir 6, is supplied to a venous reservoir 8 where air entrapped in the blood is separated by allowing the air to rise to the surface of the blood in the reservoir 8. The separated air is vented to atmosphere through an exhaust line 9.

The blood supplied by pump means 1 to the oxygenator 3 is supplied from the oxygenator 3 to an arterial filter 10 and further to the arterial line 4. The arterial filter 10 is basically a bubble trap for separating bubbles from the blood and discharging the air of the bubbles to atmosphere through an exhaust line 11.

Figure 2:
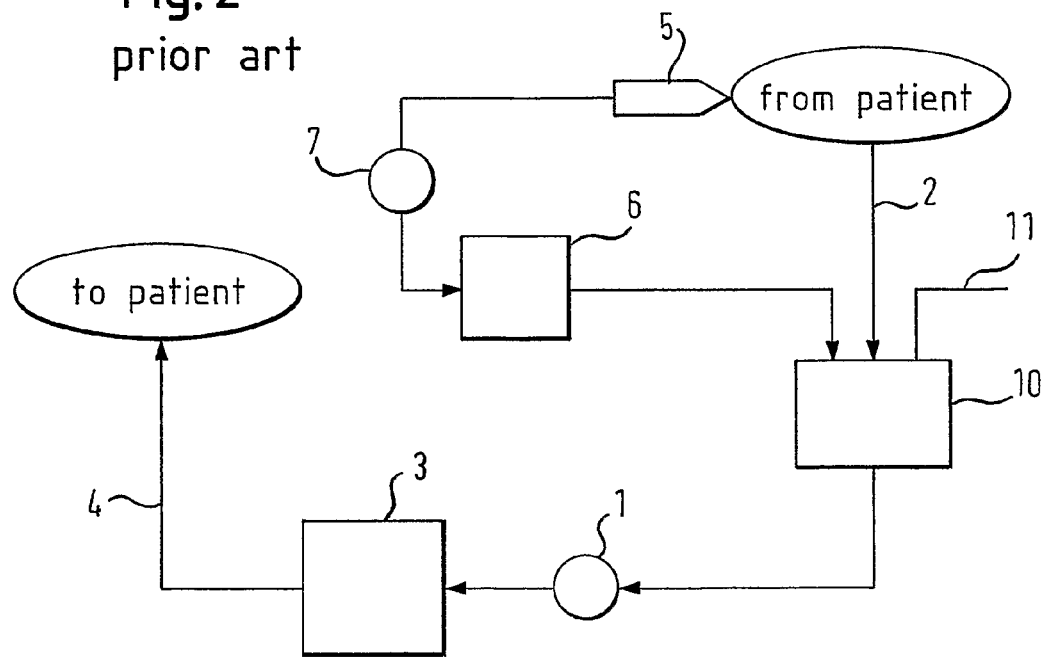
FIG. 2 is a schematic diagram of a second conventional apparatus for extracorporeal oxygenation of a patient's blood.

To avoid the venous reservoir 8 in order to reduce the priming volume of the extracorporeal blood circuit, it has been proposed, as shown in FIG. 2, to provide a bubble trap filter 10 in the venous line 2 upstream of the pump means 1. The venous blood and the blood from the suction means 5 is supplied to the bubble trap filter 10. The air separated from the blood supplied to the bubble trap filter 10 is discharged to atmosphere via exhaust line 11. The blood is pumped from the bubble trap filter 10 to the oxygenator 3 and further to the patient via arterial line 4. The negative pressure generated by the pump means 1 assists to draw blood from the patient into the bubble trap filter 10.

Figure 3:
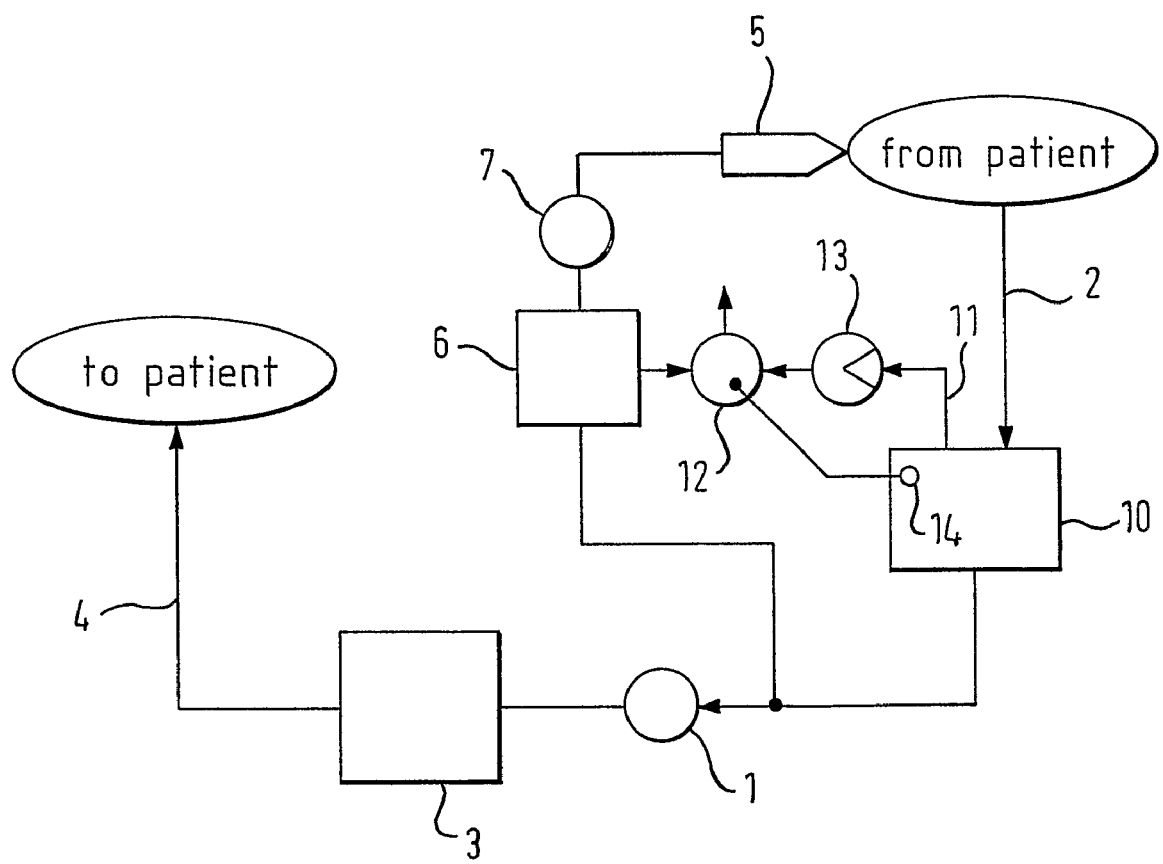
FIG. 3 is a schematic diagram of a third conventional apparatus for extracorporeal oxygenation of a patient's blood.

Alternatively, as shown in FIG. 3, it has been proposed to supply the blood of the bubble trap filter 10 and of the cardiotomy reservoir 6 to pump means 1 for being pumped to the oxygenator 3 and to the patient via arterial line 4. Further, a modification of conventional bubble trap filters has been proposed to connect further pump means 12 to the bubble trap filter 10 to draw air from the bubble trap filter 10 via an adapted exhaust line 11. The same further pump means 12 are proposed to draw air also from the cardiotomy reservoir 6. To prevent air or blood from being drawn from the cardiotomy reservoir 6 into the bubble trap filter 10, a check valve 13 is provided in the modificated bubble trap filter 10 to be arranged in the exhaust line 11 upstream of the further pump means 12. Further, an air sensor 14 is provided in the modificated bubble trap filter 10 and is connected to activate said further pump means 12 when, and only when, air is present in the bubble trap filter 10.

Figure 4:
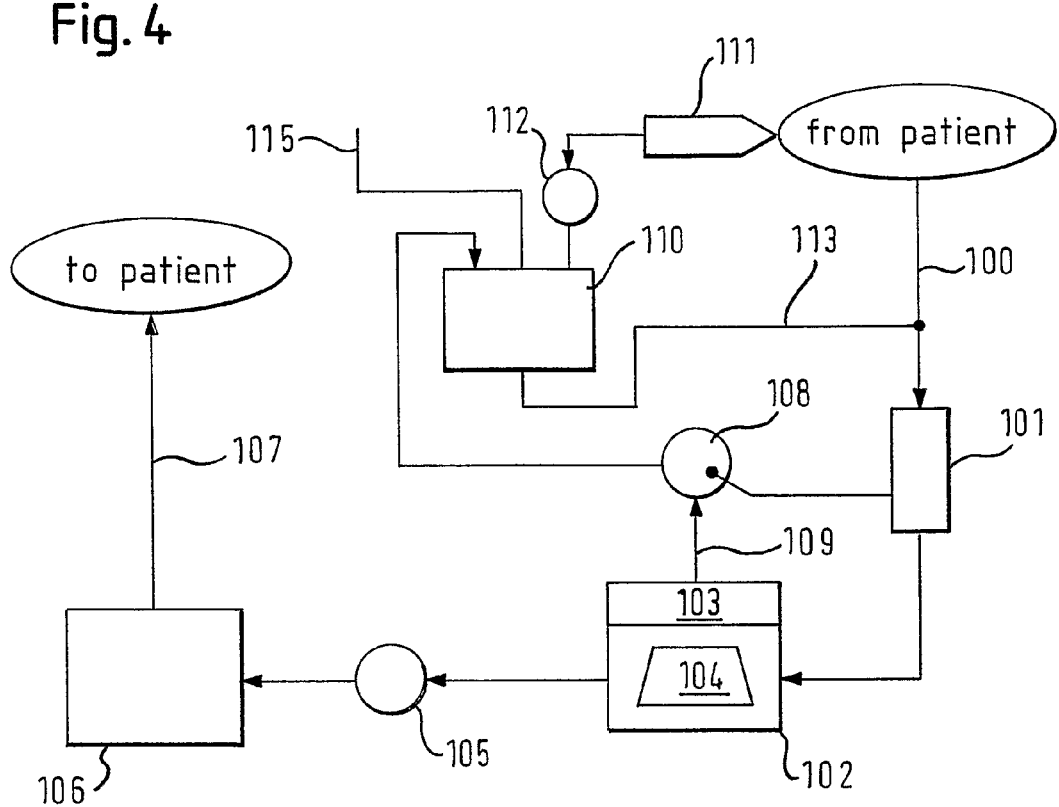
FIG. 4 is a schematic diagram of a first apparatus for extracorporeal oxygenation of a patient's blood according to the invention.

According to the invention described herein, as shown in FIG. 4, the improved apparatus for extracorporeal oxygenation of a patient's blood during cardiopulmonary bypass surgery comprises a venous line 100 for receiving venous blood from a patient and a bubble sensor 101 for detecting bubbles in the venous blood in the venous line 100. An air filter or bubble trap filter 102 is connected to the venous line 100 downstream of the bubble sensor 101 and comprises an air chamber 103 for receiving air and diverting means 104 for diverting the air entering the filter 102 into the air chamber 103. A first pump 105, defining a first vacuum, draws the blood through the venous line 100 from the air filter 102 and supplies the blood to oxygenator 106 and to the patient via arterial line 107.

The bubble sensor 101 is arranged to activate a second pump 108, defining a second vacuum, for drawing air from the air chamber 103 of the air filter 102 via exhaust line 109. The second pump 108 is activated for a predetermined time, for example 5 seconds, when bubbles are detected in the venous blood, i.e. when the bubble sensor 101 generates a signal indicating the presence of bubbles in the venous blood. Due to the second vacuum, air diverted into the air chamber of air filter 102 is drawn from the air chamber 103 and preferably supplied to a cardiotomy reservoir 110 receiving also the blood from a suction device 111 via suction pump 112.

The filtered and defoamed blood from the cardiotomy reservoir 110 is supplied to venous line 100 through supply line 113 due to the first vacuum defined by first pump means 105.

In the above arrangement according to the invention conventional components can be used to assemble the improved apparatus for extracorporeal oxygenation of a patient's blood described herein. Especially, a conventional air filter or bubble trap filter can be employed together with a bubble sensor for the controlling of the activation of a pump to actively draw air from the air filter or bubble trap filter in order to automatically remove the air.

Figure 5:
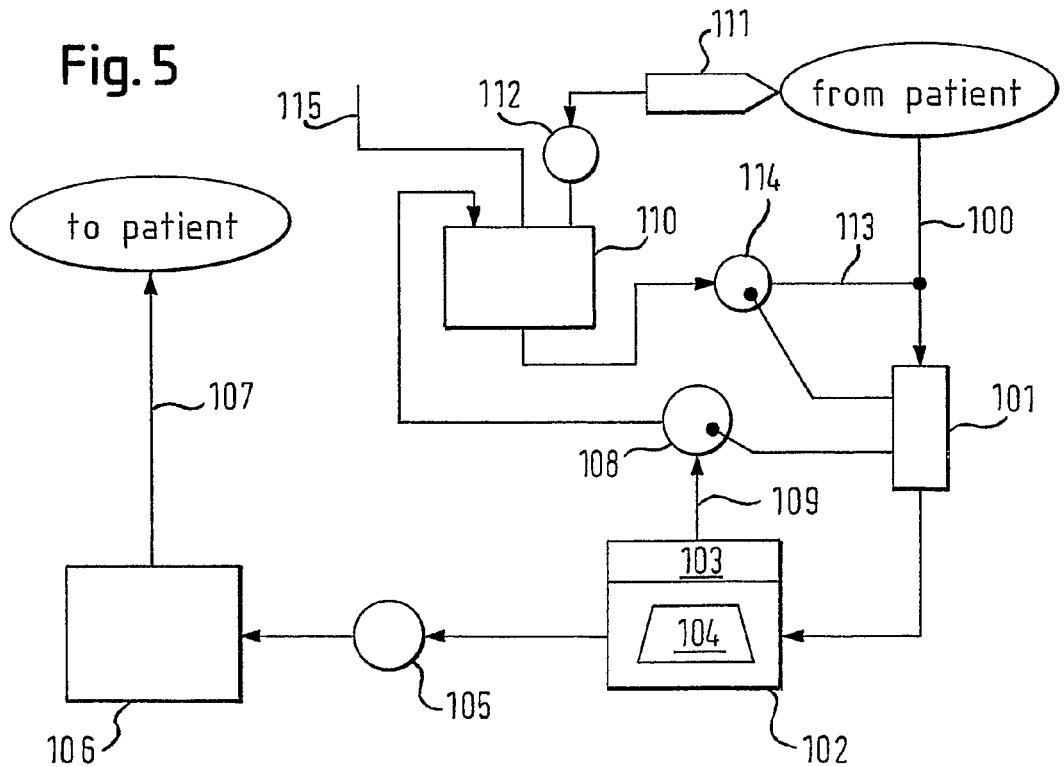
FIG. 5 is a schematic diagram of a second apparatus for extracorporeal oxygenation of a patient's blood according to the invention.

An alternative embodiment of the apparatus according to the invention is schematically show in FIG. 5 which largely corresponds to FIG. 4 so that the repeated description of corresponding aspects can be omitted by reference to the above description relating to FIG. 4. The apparatus shown in FIG. 5 further comprises a third pump 114, defining a third vacuum, arranged in the supply line 113 to actively draw blood from the cardiotomy reservoir 110 and supply the blood to venous line 100. The bubble sensor 101 is adapted to activate for a predetermined time also the third pump 114 when bubbles are detected in the venous blood, i.e. when the bubble sensor 101 generates a signal indicating the presence of bubbles in the venous blood. Due to the third vacuum, the supply of blood to the venous line 100 is assisted and not only caused by the first vacuum defined by the first pump 105.

In both embodiments of FIGS. 4 and 5, a fourth vacuum is preferably applied to exhaust line 115 of the cardiotomy reservoir 110 for drawing air from the reservoir.

It is understood that the exemplary apparatus described herein and shown in FIGS. 4 and 5 of the drawings represents only a presently preferred embodiment of the invention. Various modifications and additions may be made to such embodiment without departing from the spirit and scope of the invention. Other modifications and additions may be obvious to those skilled in the art and may be implemented to adapt the present invention for use in a variety of different applications.

The invention claimed is:

1. Apparatus for extracorporeal oxygenation of a patient's blood during cardiopulmonary bypass surgery, the apparatus comprising:
    a venous line constructed and arranged to receive venous blood from a patient;
    a bubble sensor, arranged at or connected to said venous line, that is constructed and arranged to detect bubbles in the venous blood received from the patient;
    an air filter, connected to said venous line and arranged downstream of said bubble sensor, that is constructed and arranged to separate air from blood, said air filter including an air chamber adapted to receive air and a diverter constructed and arranged to divert the air entering said air filter into said air chamber;
    a blood oxygenator constructed and arranged to oxygenate blood-after passing through said air filter;
    an arterial line constructed and arranged to return blood to the arterial system of the patient after the blood has been oxygenated by said blood oxygenator;
    a first pump constructed and arranged to generate a first vacuum to pump blood through said venous line, said air filter, said blood oxygenator and said arterial line; and
    a second pump constructed and arranged to generate a second vacuum to draw air from said air chamber of said air filter only when bubbles are detected in the venous blood by said bubble sensor, said second pump including an outlet port that is connected to a cardiotomy reservoir, said cardiotomy reservoir being connected to said venous line upstream of said bubble sensor.

2. The apparatus according to claim 1, further comprising a third pump constructed and arranged to generate a third vacuum which is to be applied to said cardiotomy reservoir to draw blood from said cardiotomy reservoir and to supply blood from said cardiotomy reservoir to said venous line.

3. The apparatus according to claim 2, further comprising a fourth vacuum source constructed and arranged to generate a fourth vacuum that is to be applied to said cardiotomy reservoir to draw air from said cardiotomy reservoir.

4. The apparatus according to claim 1, wherein said bubble sensor is connected to said second pump, said bubble sensor constructed and arranged to actuate said second pump only when bubbles are sensed in the venous blood.

* * * * *